(12) United States Patent
Maier

(10) Patent No.: US 7,330,747 B2
(45) Date of Patent: *Feb. 12, 2008

(54) INVASIVE CHEMOMETRY

(75) Inventor: John S. Maier, Pittsburgh, PA (US)

(73) Assignee: ChemImage Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/267,913

(22) Filed: Nov. 3, 2005

(65) Prior Publication Data

US 2006/0276713 A1    Dec. 7, 2006

Related U.S. Application Data

(63) Continuation-in-part of application No. 11/146,458, filed on Jun. 7, 2005.

(51) Int. Cl.
*A61B 5/00* (2006.01)

(52) U.S. Cl. ...................................... 600/322

(58) Field of Classification Search ................ 600/310, 600/322, 475, 478
See application file for complete search history.

(56) References Cited

U.S. PATENT DOCUMENTS

| | | | |
|---|---|---|---|
| 4,660,151 A | 4/1987 | Chipman et al. | |
| 4,701,838 A | 10/1987 | Swinkels | |
| 4,766,551 A | 8/1988 | Begley | |
| 4,885,697 A | 12/1989 | Hubner | |
| 5,121,337 A | 6/1992 | Brown | |
| 5,121,338 A | 6/1992 | Lodder | |
| 5,124,932 A | 6/1992 | Lodder | |
| 5,243,983 A | 9/1993 | Tarr et al. | |
| 5,280,788 A | 1/1994 | Janes et al. | |
| 5,293,872 A * | 3/1994 | Alfano et al. | 600/475 |
| 5,311,445 A | 5/1994 | White | |
| 5,341,805 A | 8/1994 | Stavridi et al. | |
| 5,372,135 A | 12/1994 | Mendelson et al. | |
| 5,481,113 A | 1/1996 | Dou et al. | |
| 5,481,476 A | 1/1996 | Windig | |
| 5,492,118 A | 2/1996 | Gratton et al. | |
| 5,536,664 A | 7/1996 | Switalski et al. | |
| 5,553,615 A | 9/1996 | Carim et al. | |
| 5,715,816 A | 2/1998 | Mainiero et al. | |
| 5,974,338 A * | 10/1999 | Asano et al. | 600/323 |
| 5,983,120 A * | 11/1999 | Groner et al. | 600/310 |
| 6,061,583 A * | 5/2000 | Ishihara et al. | 600/322 |
| 6,070,093 A | 5/2000 | Oosta et al. | |
| 6,353,750 B1 * | 3/2002 | Kimura et al. | 600/344 |
| 2002/0033454 A1 | 3/2002 | Cheng et al. | |

(Continued)

FOREIGN PATENT DOCUMENTS

WO    WO 2004/008089 A1    1/2004

*Primary Examiner*—Eric Winakur
*Assistant Examiner*—Etsub D Berhanu
(74) *Attorney, Agent, or Firm*—Morgan, Lewis & Bockius, LLP

(57) ABSTRACT

The invention relates to methods and devices for assessing one or more components of a selected tissue in an animal. The present invention permits non-invasive assessment of tissue components in a body structure containing multiple tissue types by assessing multiple regions of the animal's body for an optical characteristic of the tissue of interest and separately assessing one or more optical (e.g., Raman or NIR) characteristics of the tissue component for one or more regions that exhibit the optical characteristic of the tissue of interest.

18 Claims, 6 Drawing Sheets

U.S. PATENT DOCUMENTS

| | | |
|---|---|---|
| 2003/0139667 A1* | 7/2003 | Hewko et al. ............... 600/410 |
| 2003/0176777 A1 | 9/2003 | Muller-Dethlefs |
| 2004/0157208 A1 | 8/2004 | Ling et al. |
| 2005/0043597 A1 | 2/2005 | Xie |
| 2006/0129037 A1 | 6/2006 | Kaufman et al. |
| 2006/0276697 A1 | 12/2006 | Demuth et al. |

* cited by examiner

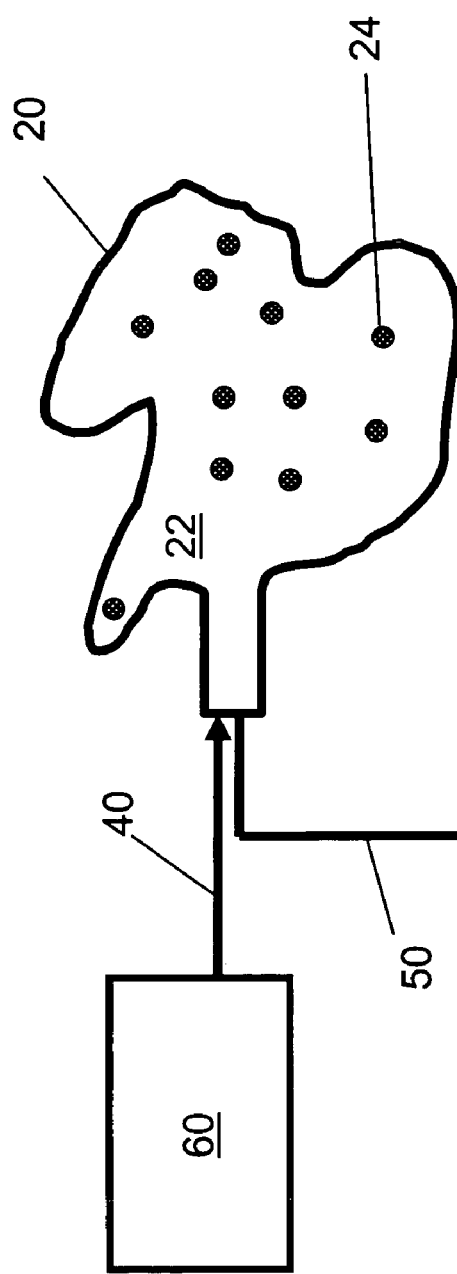
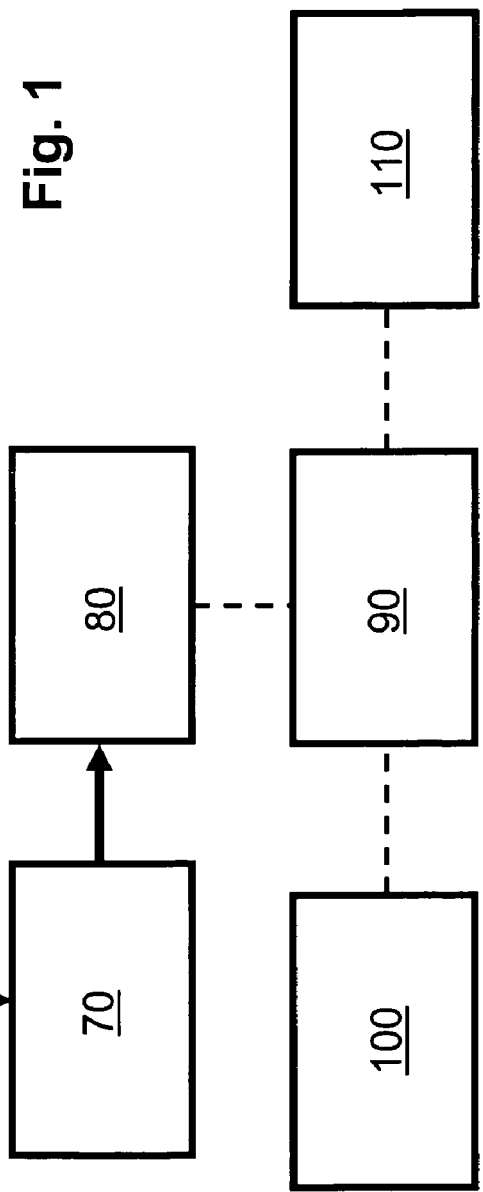
Fig. 1

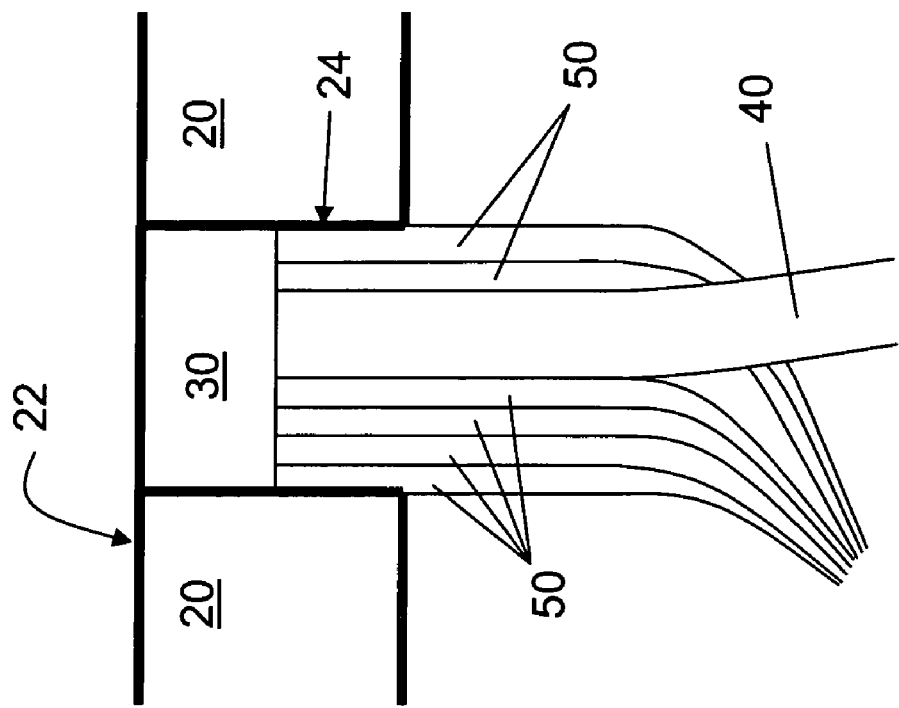
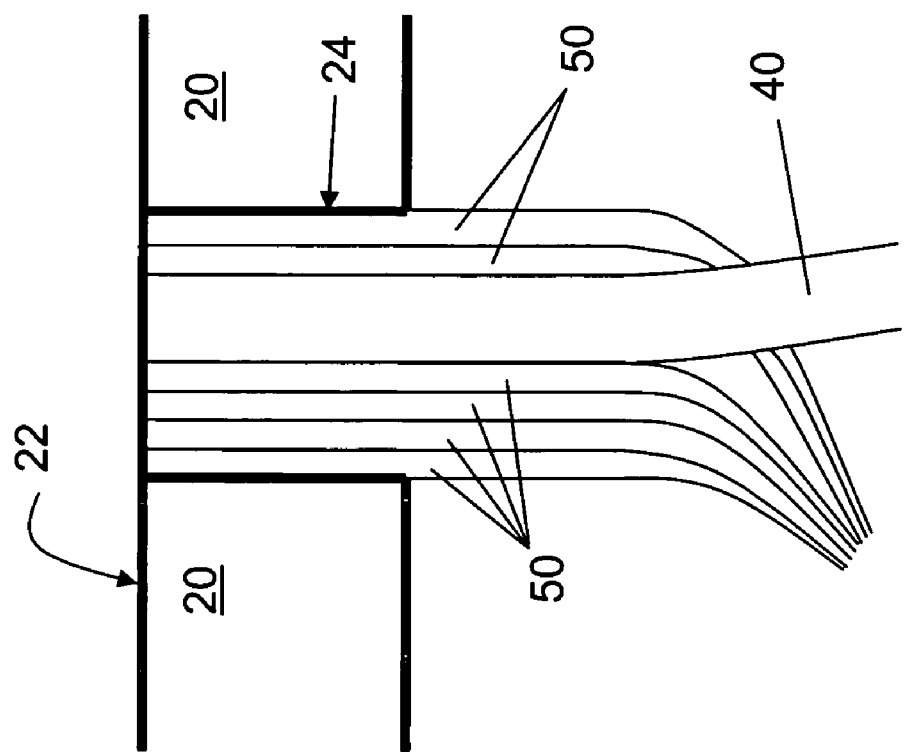

INVASIVE CHEMOMETRY

CROSS-REFERENCES TO RELATED APPLICATIONS

This application is a continuation-in-part of co-pending U.S. application Ser. No. 11/146,458, which was filed on 7 Jun. 2005, the entire contents of which are incorporated herein by reference.

BACKGROUND OF THE INVENTION

The invention relates generally to the field of in vivo chemometric analyses of chemical components of cells, tissues, or organs in a living organism.

Analyses of the chemical composition of blood and other tissues are among the most commonly performed medical diagnostic techniques. Typically, such analyses are performed by obtaining a sample of the tissue to be analyzed from a patient (e.g., by drawing blood or by performing a biopsy) and thereafter subjecting the sample to various analytical techniques. Such invasive techniques have disadvantages including discomfort to the patient during sample collection, inconvenience of sample collection, and the possibility that collected samples can be lost or misidentified. Discomfort and inconvenience are magnified in situations in which frequent or regular sample collection is required, such as with blood glucose determinations for diabetic patients.

Various analytical chemical techniques are known for quantitation of individual chemical species, but most such techniques quantify only one or a few chemical species independently or one at a time. Among other analytical techniques that are known are a variety of spectral techniques, including those involving absorbance, transmittance, reflectance, emission, and scattering (elastic and non-elastic) of radiation applied to a sample. For example, Raman scattering analysis of whole blood has been described (Enejder et al., 2002, Optics Lett. 27(22):2004-2006) and is suitable for clinical quantitation of blood glucose, dissolved oxygen, dissolved carbon dioxide, urea, lactic acid, creatine, bicarbonate, electrolytes, protein, albumin, cholesterol, triglycerides, hematocrit, and hemoglobin. Spectral techniques, such as Raman spectral analysis, have the advantage that multiple chemical species can be quantified simultaneously, so long as the species can be spectrally distinguished.

Others have described analytical devices and techniques intended for non-invasive in vivo analysis of tissue components. However, each of these has certain disadvantages and limitations. For example, each of Berger et al. (U.S. Pat. No. 5,615,673) and Yang et al. (U.S. Pat. No. 6,167,290) describes a Raman spectroscopic system designed for transdermal analysis of blood components. Xie (U.S. Patent Application Publication No. 2005/0043597) describes a spectral analysis system intended to analyze blood components using radiation passed across a nail of a finger or toe. In each of these instances, individual variation in skin or nail properties and in blood vessel placement can significantly affect the utility of the devices and methods.

A need exists for systems and methods for non-invasive compositional analysis of human tissues, particularly including blood. The present invention satisfies this need.

BRIEF SUMMARY OF THE INVENTION

The invention relates to method of assessing one or more components of an animal tissue (e.g., a human tissue), either in vitro or in vivo. The method includes assessing multiple irradiated regions of an animal body to identify at least one region that exhibits a first optical characteristic of the tissue. A second optical characteristic of the component (e.g., a Raman shift characteristic of the component) is assessed for at least one identified region (and preferably for multiple regions identified as exhibiting the first optical characteristic). In this method, interfering signals from the same or a different component in a tissue other than the tissue of interest can be reduced or avoided. In some embodiments, one or more confirmatory optical characteristics of the tissue can be assessed at the identified regions to confirm that the individual identified regions correspond to the tissue of interest. The second optical characteristic of the component can, if desired, be assessed only at identified regions that exhibit the confirmatory optical characteristic.

A variety of devices can be used to perform the assessment methods described herein. By way of example, the methods can be performed using a device wherein the first optical characteristics of the irradiated regions are assessed using multiple optical conduits (e.g., plastic-clad optical glass fibers). These conduits optically couple the irradiated regions with a detector. If desired, the conduits can optically couple individual irradiated regions with different detector elements of the detector. If an image of the assessed regions of the animal body is desired, then the arrangement of the optical conduits can be controlled, using a coherent bundle of optical fibers, for example.

If the assessed body regions are accessible from a surface of the animal, then the conduits can simply be pressed against, or maintained in close opposition to, the surface. Alternatively, the conduits can extend along a probe inserted into the body of the animal or applied against a body surface of the animal. Any of a wide variety of known probe-type devices can be used, including probes in which optical conduits are fixedly attached to the probe body and those in which the optical conduits (or a sub-assembly including the optical conduits) can be moved within the probe body such that the detection end of each optical conduit can be used to assess multiple body regions without moving the probe body. By way of example, the optical conduits can fixedly or movably disposed within a catheter, a cannula, or an endoscope (e.g., an arthroscope, a bronchoscope, a thoracoscope, a colonoscope, a sigmoidoscope, a duodenoscope, a gastroscope, a pancreatoscope, a choledochoscope, a nasopharyngoscope, a rhinolaryngoscope, a laparoscope, or a colposcope).

In one embodiment, the optical conduits are rigidly fixed relative to one another (e.g., the optical conduits are fused or enclosed within an optically clear jacket). Such fixation of conduits to one another can improve the rigidity and durability of the conduits and can enhance the coherence of the image produced using the conduits, in coherent imaging systems. Significantly, the collection axes of the optical conduits need not necessarily be substantially parallel, as in an imaging device. At least in embodiments in which a coherent image of the assessed body regions is not required, there need not be any particular relationship among the collection axes of the conduits. The axes can be substantially parallel, in dispersed parallel bundles, or irregularly arranged. Because the first and second optical characteristics are collected using the same optical fiber for any particular body location, there need be no particular geometric arrangement among the conduits.

The method described herein can be used to assess a wide variety of components in animal tissues, either individually or substantially simultaneously. The components can be individual chemical species (e.g., one or more of glucose, dissolved oxygen, dissolved carbon dioxide, urea, lactic acid, creatine, bicarbonate, an electrolyte, protein, cholesterol, triglycerides, lipids other than triglycerides, and hemoglobin). The methods can also be used to assess cells in a tissue, and to distinguish normal and abnormal cells (or to detect the presence of abnormal cells, such as cancer cells). Substantially any component having one or more optical characteristics by which it may be identified can be assessed in an animal tissue using the methods described herein.

Device useful for assessing a component of a tissue of an animal as described herein should have a detector capable of identify regions of an animal body that exhibits a first optical characteristic of a tissue of interest when the regions are irradiated. The device should also have a detector capable of assessing a second optical characteristic of the component of interest in those body regions identified as corresponding to the tissue of interest. The same detector can be used for both functions, or separate detectors can be used. The device should include a controller for limiting assessment of the second optical characteristics to the identified regions. Preferably, the device also includes optical conduits which transmit light reflected, transmitted, emitted, or scattered by or from the body regions to one or both of the detectors. Although the device need not include a radiation source for generating the light to be reflected, transmitted, scattered, or absorbed and re-emitted by the tissues and components, it is preferable that a controlled (e.g., monochromatic) light source be used, and such a light source (e.g., a laser) can be incorporated into the device. In one embodiment, optical illuminating fibers are used to transmit light from the light source to the tissue(s) and component(s) being assessed and a separate set of optical detection fibers are used to transmit light from the tissue(s) and component(s) to the detector(s). One or more optical filters or other light-manipulating elements can be interposed among the other optical components. By way of example, an optical filter that reduces or substantially prevents transmission of light having the same wavelength as that used to illuminate the sample can be used to distinguish Raman scattered light from illuminating light.

BRIEF SUMMARY OF THE SEVERAL VIEWS OF THE DRAWINGS

FIG. 1 is a schematic diagram of an embodiment of the non-invasive device described herein.

FIG. 5, comprising FIGS. 5A and 5B, is a diagram illustrating a detail of two embodiments of the device described herein.

DETAILED DESCRIPTION OF THE INVENTION

Figure 2:
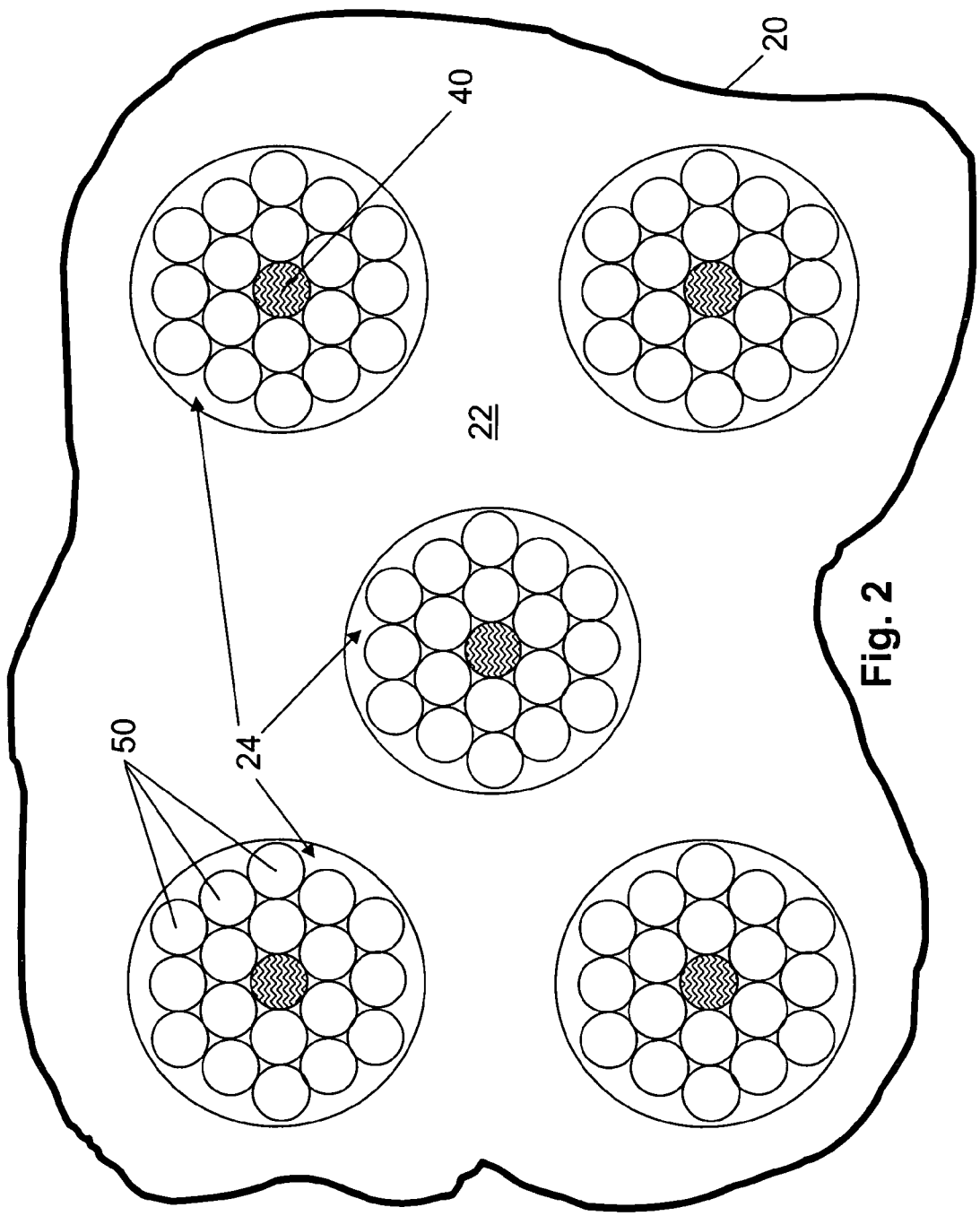
FIG. 2 is an example of a layout pattern for optical fibers and holes in a device described herein.

The invention relates to methods and devices for assessing one or more components of a tissue in an animal. Prior analytical methods required biopsy and isolation of the desired tissue and subsequent analysis. The present invention permits assessment of tissue components without removal of the tissue from the animal body and without isolation of the tissue or components from other tissues or components with which it may be interspersed.

Crudely simplified, the methods described herein involve assessing an optical property (e.g., reflectance of a particular wavelength of light) for multiple regions of a portion of an animal's body, whether external or internal. Regions of the body which exhibit an optical characteristic of one or more desired tissue types are selected for assessment of one or more additional optical characteristics (e.g., Raman spectral characteristics). These additional characteristics can be selected to provide information about the presence, concentration, or oxidation state (for example) of one or more components of the animal's blood. Further by way of example, the methods and devices described herein can be used by inserting a probe into an animal's body. Multiple optical conduits on the probe can be used to irradiate multiple portions of the body, and other optical conduits can be used to collect radiation reflected, transmitted, emitted, or scattered by irradiated portions the body. Analysis of that collected radiation can indicate the type(s) of tissue from which the individual conduits are collecting radiation, and those conduits can be used to collect radiation for which the optical characteristics are informative of the presence, absence, state, or concentration of a component of a tissue of interest.

These methods can be practiced using a device that optically analyzes multiple regions of the body. The device is capable of detecting the optical characteristic of tissues in an addressable manner, so that the device can distinguish regions based on the presence, absence, magnitude, or rate of change of the characteristic. The device can thereby identify regions of the body at which the tissue of interest is present. The device is also capable of detecting an optical characteristic of a component of a tissue of interest for each of the multiple regions, thereby assessing the presence, absence, or relative concentration of the component for each region. By combining these two capabilities, the device can assess the tissue component present at or near regions of the body that include the tissue (and can disregard optical characteristics of other components and tissues). As a result, noise, weak signals, and signals arising from compounds in tissues other than the tissue of interest can be avoided, and a signal corresponding to the desired component in the tissue of interest can be analyzed.

Definitions

As used herein, each of the following terms has the meaning associated with it in this section.

A "tissue" of an animal body means a collection of cells and/or extracellular materials that form a discernable body structure. In this sense, the word tissue is used in its usual sense in the medical arts, including structures composed almost entirely of living cells, structures composed almost entirely of non-living materials, and structures composed of a mixture of living cells and non-living materials. Non-limiting examples of tissues include epithelia, muscle, liver, blood, serum, bone, tendon, nerve, brain, and skin.

"Bandwidth" means the range of wavelengths in a beam of radiation, consistent with a specified full width at half maximum.

"Bandpass" of a detector or other system means the range of wavelengths that the detector or system can distinguish (i.e., transmit or permit to pass through its optics), as assessed using the full width at half maximum intensity method.

The "full width at half maximum" ("FWHM") method is a way of characterizing radiation including a range of wavelengths by identifying the range of contiguous wavelengths that over which the magnitude of a property (e.g., intensity or detection capacity) is equal to at least half the maximum magnitude of that property in the radiation at a single wavelength.

An "optical characteristic" of a compound or tissue property is an optical property of the compound or tissue by which the compound or tissue can be distinguished from other compounds or tissues that occur together with the compound or tissue of interest. By way of example, an optical characteristic of blood is an optical property (e.g., absorbance or reflectance in the red-to-near infrared (NIR) region of the electromagnetic spectrum) that can be used to differentiate blood or a blood-rich tissue from tissues which contain little or no blood near a vascularized surface of an animal. Similarly, an optical property of a blood component such as glucose is an optical property (e.g., a Raman or NIR spectrum) of a component of blood that can be used to differentiate the component from other blood components.

A "region" in a sample refers to a relatively small area of an illuminated surface of an animal. For example, regions can have sizes of 0.01-1 square millimeter. The geometry of the area corresponding to a region is not critical. For example, a region can refer to a circular, annular, or square area of a surface. A region can be as small as the area of a surface from which light is collected by a single optical fiber or by a bundle of optical fibers (e.g., areas as small as a few square microns).

The terms "optical" and "spectroscopic" are used interchangeably herein to refer to properties of materials (and to methods of assessing such properties). The term "spectroscopic" is generally understood to refer to the interaction of electromagnetic radiation, electrons, or neutrons with the materials. The term "optical" typically refers to an interaction with electromagnetic radiation. For example, although electron microscopy is not always commonly considered a "spectroscopic" or "optical" method, the two terms are used inclusively herein to encompass electron microscopy and other methods of assessing interaction of a material with visible, ultraviolet, or infrared light, with neutrons, or with other radiation.

The terms "light" and "radiation" are used interchangeably herein to refer to electromagnetic radiation having wavelengths associated with ordinary spectrographic techniques, such as radiation in the ultraviolet (UV), visible, near infrared (NIR), and infrared (IR) regions of the spectrum. In particular, the term "light" is not limited to radiation in the visible portion of the spectrum.

In the context of this application, an "optically clear" material is one which does not significantly inhibit transmission through the material of radiation having a wavelength corresponding to an optical characteristic of interest for a tissue of interest or for an analyzed component of that tissue.

"Spectral resolution" means the ability of a radiation detection system to resolve two spectral peaks.

"Quantification" of an optical characteristic of a compound means assessment of the value of the characteristic with a greater precision than mere observation of the presence or absence of the compound. Quantification includes, for example, assessment of the characteristic with sufficient precision that an approximate concentration of the compound in a medium can be determined from a standard curve or assessment that the characteristic for one composition is greater or less than the characteristic for another composition.

Detailed Description

The invention relates to methods and apparatus for assessing a component of one or more tissues of an animal. The methods involve assessing the optical properties of irradiated portions of an animal body in order to identify one or more regions of the body at which the optical properties of the tissue(s) of interest are evident. After those portions have been identified, an optical property of the compound of interest is assessed at some or all of those portions.

In one embodiment of the invention, multiple optical fibers are contacted with (or brought into close opposition with) multiple portions of a tissue that includes multiple cell types (e.g., the liver). The portions are irradiated, and radiation collected from the optical fibers is analyzed to identify the portions which exhibit a first optical characteristic of a desired cell type (e.g., hepatocytes). Radiation transmitted from those identified portions by way of the optical fibers can be analyzed for a second optical characteristic of a component of interest (e.g., glucose). By limiting assessment of the second optical characteristic to optical fibers transmitting radiation from the identified portions (i.e., from hepatocytes), glucose content in hepatocytes can be assessed, despite the fact that hepatocytes are not the only cell type in liver tissue that contain glucose. Similarly, glucose content of red blood cells, leukocytes, Kupffer cells, blood serum, or lymph in liver tissue can be assessed using the same optical fiber probe—by analyzing the second optical characteristic (that of glucose) using fibers which exhibit a first optical characteristic of the tissue for which glucose analysis is desired.

In another example of an embodiment of the invention, blood glucose concentration for a human can be measured by assessing visible light scattered from multiple regions of a vascularized surface, such as skin or an oral inner cheek surface, to identify blood-rich portions (e.g., portions of the surface at which a blood vessel lies very near the surface). Raman-shifted radiation scattered from those portions can be assessed at Raman shift values characteristic of glucose and compared with reference values to estimate glucose content in the blood. The methods and devices are not limited to detection of blood glucose. Substantially any optically-detectable component of blood can be assessed using the methods and apparatus described herein.

An important aspect of the invention is that a first optical property is assessed at multiple regions of the body to identify the location of regions which exhibit one or more optical properties of a tissue of interest. By limiting assessment of an optical property of a tissue component to these regions, signal strength can be improved and noise and interference from cells, tissues, and compounds other than the component of interest in the tissue of interest can be reduced.

Another important aspect of the invention is that the methods can be performed either invasively or non-invasively. Substantially any animal surface can be used, so long as it has the tissue of interest sufficiently close to the surface that one can assess optical properties of the tissue and component of interest using a non-invasive probe. Because optical conduits (e.g., plastic-clad optical glass fibers) can be made exceedingly small, such conduits can be inserted into and through spaces, tissues, and fluids of animal bodies in a relatively minimally invasive manner in order to assess portions of the body that are not readily accessible using a probe applied to a body surface. The availability of highly sensitive detectors (e.g., charge-coupled device (CCD) detectors) and the ability of certain wavelengths of radiation to penetrate tissues without substantial absorption permit the methods described herein to assess tissue components in tissue located as far from a surface as the non-injurious intensity and absorbance of the radiation permits. By way of example, visible light can be used to assess tissue components tens or hundreds of micrometers from a surface, and infrared (e.g., including at least mid- and near-infrared light) can be used to assess tissue components millimeters or centimeters distant from a surface.

The methods and apparatus described herein can be used to assess substantially any component of a tissue that can be spectrally distinguished from other tissue components, either directly or indirectly. A tissue component can be assessed directly if it exhibits at least one optical characteristic whereby it can be spectrally distinguished from other tissue components. A tissue component can be indirectly assessed if an optical characteristic that can be spectrally distinguished from optical characteristics of other tissue components can be associated with the component. By way of example, a fluorescently-labeled antibody can be introduced into the tissue of a patient, whereupon the antibody binds with a protein which bears an epitope to which the antibody binds. Fluorescently-labeled proteins are thereby created, and those proteins can be detected using the methods described herein. Similarly, a compound that is selectively taken up by cells of a certain type can be used for indirect assessment of such cells. Other indirect cell- and compound-labeling techniques are known in the art, and substantially any of those techniques can be used in conjunction with the methods described herein.

Examples of tissue components that can be assessed using the methods and devices described herein include whole cells (e.g., normal, cancerous, or other diseased cells), extracellular matrix materials (e.g., collagens, atherosclerotic and other plaques, calcifications, bone matrix, and materials of exogenous origin such as plastic or metal fragments), and normal cellular components (e.g., glucose, dissolved oxygen, dissolved carbon dioxide, urea, lactic acid, creatine, bicarbonate, electrolytes, proteins, nucleic acids, cholesterol, triglycerides, and hemoglobin).

The methods and devices described herein are essentially equally applicable to human and animal systems, the adaptations necessary for veterinary applications being readily evident to and capable of being made by an ordinary veterinarian.

Suitable Body Portions

The methods and devices described herein can be used to assess a tissue component in substantially any body location, whether that location is readily accessible from the outside of the animal or is deep within the interior of the animal. Any body location which can be irradiated and from which transmitted, reflected, emitted, or scattered radiation can be collected can be assessed using the methods and devices described herein. In view of the information provided herein, choices of analytical devices and methods for performing the invention will be evident to a skilled artisan, the particular devices and methods depending on the identity of the tissue(s) and component(s) to be analyzed. By way of example, liver tissue cannot ordinarily be accessed from the exterior of a healthy animal without making an incision, puncture, or other orifice by way of which an optical probe can be contacted with or brought into close opposition to liver tissue. Skin, for example, can normally be accessed externally without an incision or other surgically- or traumatically-created orifice.

It is not necessary that the body portion analyzed using the methods and devices described herein be composed uniformly or entirely of a single cell type. As described herein, multiple portions are assessed, and those portions which do not exhibit an optical characteristic of the tissue of interest can be identified. Analysis of the component of interest can thereby be limited to a single tissue of interest. Because multiple body portions are analyzed, the methods described herein can be used to simultaneously assess one or more components in multiple tissues present at the analyzed body portions. By way of example, a substantially cylindrical optical probe having multiple optical fiber bundles arranged therein such that the body portions from which the bundles collect radiation are circumferentially arranged (in an ordered or random manner) about the probe can be inserted into liver tissue. Some fibers or bundles will collect radiation only or substantially only from cells of a first type (e.g., hepatocytes). Other fibers or bundles will collect radiation only or substantially only from tissue of a second type (e.g., blood). Still other fibers or bundles will collect radiation only or substantially only from a fibrous or connective tissue. The same component (e.g., glucose) or different components can be assessed in these various tissue by performing the component assessment using radiation collected by the corresponding fibers or bundles.

Vascularized Animal Surfaces

In one embodiment, the methods and devices described herein can be used to assess a blood component in substantially any vascularized tissue. It is recognized, however, that tissues that are not rich in blood can obscure or obstruct radiation transmitted to or from blood tissue. For that reason, the methods and devices described herein are preferably used in connection with blood-rich tissues (e.g., arteries, veins, capillaries, and spaces in which blood can pool) and preferably avoid, to the extent practical, tissues that are not rich in blood. Tissues that contain significant amounts of connective tissue between a blood-rich tissue and the detector described herein are preferably avoided.

Preferred tissue surfaces for assessment of blood components using the methods and devices described herein are those which are vascularized and in which the vascularization is located relatively near the surface of the tissue. Although the methods described herein can be performed using ordinary skin tissue (e.g., the tissue on the inner surface of the forearm or wrist), it is recognized that the keratinized surface of skin, its connective-tissue rich dermal layer, and melanin and other skin pigments can interfere with the methods. Non-dermal epithelia (e.g. an epithelium with a thin, or no, dermal layer underlying it) are preferred surfaces for the assessment methods described herein. Likewise, epithelia that overlie vascularized tissue that is not covered with a keratinized layer of dead cells are preferable. Preferably, the tissue surface assessed does not have a keratinized layer of dead cells, an underlying dermal layer, or significant epithelial cell pigmentation.

Non-Invasive Chemometry

In one embodiment, the methods described herein are performed non-invasively. Substantially any surface of an animal can be analyzed, contingent on the presence of the tissue of interest at or near the surface. For example, for blood analysis the apical surface (i.e., the free surface; the surface opposite the basement membrane) of a non-dermal epithelium that is accessible without puncturing or cutting a body surface is preferred for such non-invasive methods. Numerous such surfaces are accessible on the human body. These surfaces are commonly thought of as "pink tissue" surfaces, and are generally moist, highly-vascularized tissues that line body orifices and cavities. Many of these surfaces are mucosal epithelia, although vascularized surfaces (e.g., the superior surface of the tongue) that are not normally considered mucosal epithelia are also suitable.

Examples of suitable vascularized non-dermal epithelial surfaces include the floor of the mouth, the soft palate, the lingual surface of the tongue, inner cheek surfaces, the gums and gingiva, esophagus lining, stomach wall lining, intestinal and colonic linings, olfactory epithelium, pharyngeal epithelium, bronchial epithelium, alveolar epithelium, urethral epithelium, vaginal epithelium, and vulval epithelium.

There are numerous advantages of performing the methods described herein non-invasively using a vascularized non-dermal epithelial surface. In addition to limiting spectral interference and improving the signal-to-noise ratio for the desired analyte, analysis performed using a non-dermal epithelial surface can be done relatively quickly and easily and with a minimum of patient discomfort. The methods can be self-administered or administered to non-ambulatory patients.

Invasive Chemometry

The methods described herein can also be performed invasively, meaning that at least one body structure of the animal is breached in order to place the optical probe used in the methods described herein at a selected body location. The optical probe can be used to breach the tissue, in which instance, the probe should be constructed suitably ruggedly to withstand the forces of such breach without substantially losing or impairing its optical analytical functions. Alternatively, the optical probe can be directed to a body location to which access has been provided by breaching a body structure using an instrument other than the optical probe.

Figure 6:
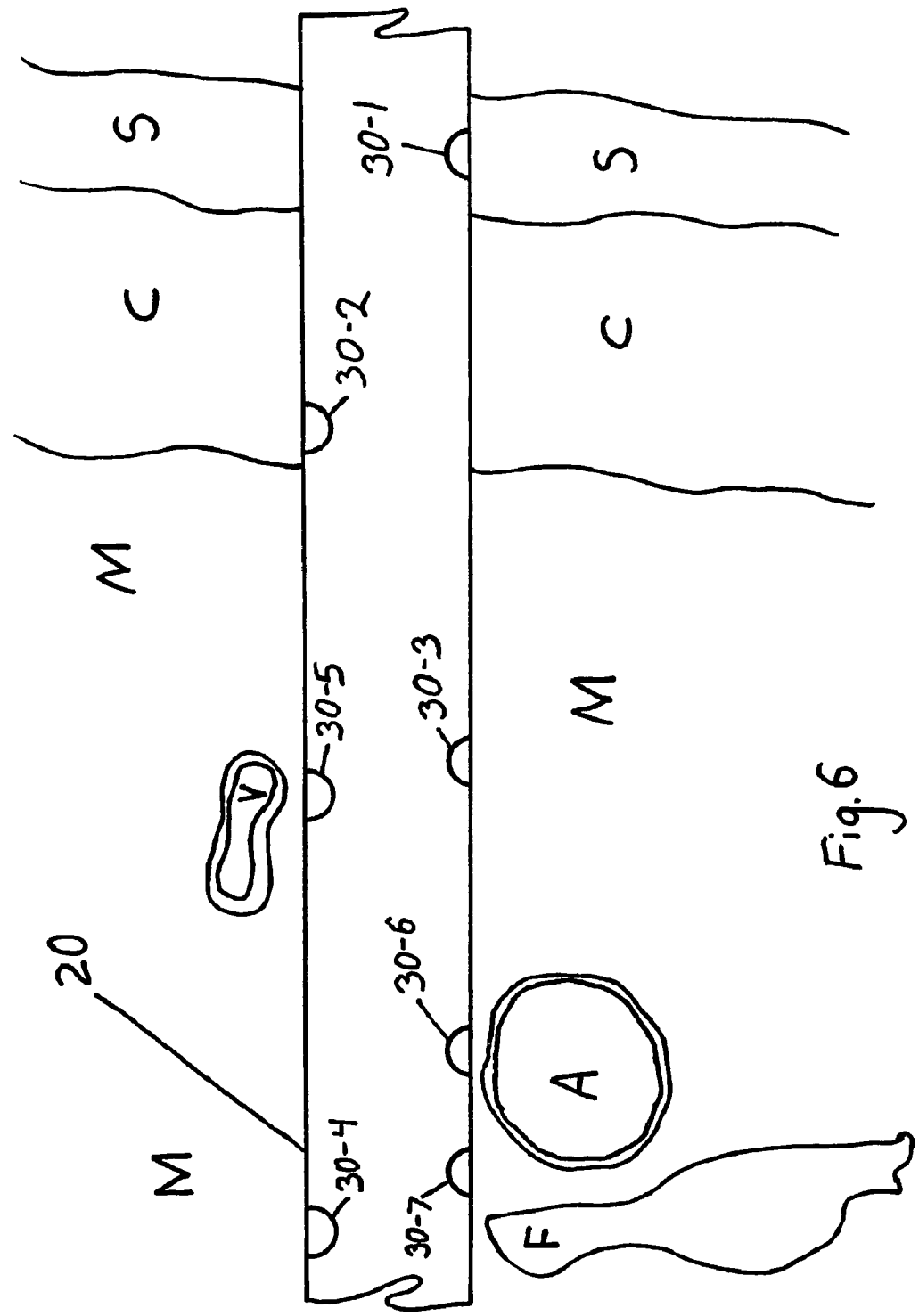
FIG. 6 is a diagram illustrating a portion of an optical probe 20 penetrating several tissues of an animal.

Use of an invasive probe has the advantage that multiple components of multiple tissues can be monitored sequentially or substantially simultaneously. The number of tissues that can be simultaneously monitored is limited by the number of tissues which can be put into contact with or close opposition to one or more optical conduits of the probe. FIG. 6 illustrates this concept. FIG. 6 is a simplified diagram showing an optical probe 20 penetrating the skin S of an animal. The probe 20 also penetrates a connective tissue C and a muscle tissue M of the animal. Lenses 30 collect radiation from tissues which the probe 20 contacts or is in close opposition to and transmit that radiation to one or more optical conduits (not shown) within the probe 20. In FIG. 6, lens 30-1 collects radiation from skin tissue S that it contacts, lens 30-2 collects radiation from connective tissue C that it contacts, lenses 30-3 and 30-4 collect radiation from muscle tissue M that they contact, lens 30-5 collects radiation from radiation from venous capillary B which lies in close opposition thereto, and lens 30-6 collects radiation from arterial capillary A which lies in close opposition thereto. As shown in FIG. 6, some lenses will collect radiation from more than one tissue type. For example, lens 30-7 collects radiation from at least the muscle tissue M, arterial capillary A (most likely including both arterial blood and capillary wall tissues), and the fatty deposit F. The tissues corresponding to the various optical fibers can be identified and distinguished by analysis of the optical characteristics of radiation collected by the lenses 30 and transmitted by way of the optical fibers.

One or more components of the devices described herein can be implanted and used in situ to monitor a tissue component, in conjunction with appropriate physical or transmitted (e.g., by radio waves) connections to the exterior of the patients body. Furthermore, the methods and devices described herein can be used with an invasive probe, such as a sheathed, drawn-optical fiber probe that pierces a tissue or is threaded along a tubular body cavity such as a blood vessel. The radiation-collecting optics corresponding to individual optical conduits or bundles of optical conduits can be arranged on the probe in an organized or random pattern. Other examples of devices suitable for use in the methods described herein include the microlens array fiber optic device described in co-pending U.S. patent application Ser. No. 10/962,662, filed 13 Oct. 2004 and the chemical imaging fiberscope described in U.S. Pat. No. 6,788,860.

Whether considered non-invasive or invasive, application of an optical probe as described herein to a body surface (e.g., the inner wall of the stomach by way of a gastroscope) is a convenient and minimally-traumatic way of performing the analysis described herein. Such analysis can be performed by using an appropriate endoscope (e.g., one of an arthroscope, a bronchoscope, a thoracoscope, a colonoscope, a sigmoidoscope, a duodenoscope, a gastroscope, a pancreatoscope, a choledochoscope, a nasopharyngoscope, a rhinolaryngoscope, a laparoscope, and a colposcope) to direct the optical probe to a body location at or near which a tissue of interest occurs. If desired, an imaging apparatus of the endoscope can be used to direct or confirm placement of the optical probe. Alternatively, a cannula, catheter, or other device having a hollow through which the optical probe can be moved can be used to place the optical probe at a desired body location or to direct the optical probe to a desired site of tissue penetration.

Radiation Source

The body location at which a tissue component is to be assessed is irradiated. The irradiation can be applied to the same side of the tissue surface from which light is collected, from the opposite side (e.g., in the case of relatively thin accessible tissues such as the oral cheek), or some combination of these.

In most instances, light from a controlled source will be used to irradiate the surface. However, use of relatively uncontrolled radiation sources such as the sun or a household incandescent light bulb is not excluded. In order to minimize variability, however, it is preferable to use light from a controlled source, such as a laser, light-emitting diode, or a filament bulb. The controlled radiation source can be adapted to the geometry and sensitivity of the devices described herein and can be selected based on the spectral properties of the tissue component being analyzed. Certain spectroscopic techniques (e.g., Raman scattering analysis) are best performed using substantially monochromatic light for irradiation of the sample. numerous suitable sources of substantially monochromatic light are known, including lasers and polychromatic light sources equipped with a diffraction grating, for example. A skilled artisan is able to select one or more appropriate radiation sources based on the optical properties of blood, the optical properties of the tissue and component of interest, and the spectroscopic technique to be used to identify each.

The analytical methods described herein involve analysis of multiple regions of a sample. Those multiple regions are assessed for at least the occurrence of an optical characteristic of the tissue of interest, and some or all of the regions can be assessed for the occurrence of at least one optical characteristic of the tissue component of interest. Preferably, a single light source is used for each of these analyses. However, multiple light sources can be used.

Each light source can be used to illuminate a portion of the sample surface that includes all of the multiple regions. Alternatively, the radiation source can be used to illuminate only, or substantially only, the regions to be assessed. The assessed regions can be irradiated simultaneously, one at a time, in a random fashion, or otherwise. For assessed regions that are determined not to exhibit an optical characteristic of the tissue of interest, irradiation can be discontinued, if desired, during analysis of regions at which the tissue of interest occurs. Alternatively, irradiation can be redirected from regions that are determined not to exhibit an optical characteristic of the tissue of interest to regions that do, in order to boost the intensity of the optical signal from regions including the tissue of interest.

Unlike prior art methods, the methods described herein avoid much of the interference and obstruction associated with keratinized and other connective tissue-rich portions of tissue surfaces. For this reason, it is not necessary, as it is with prior art methods, to select irradiation wavelengths that are not significantly absorbed by tissues other than the tissue of interest.

Irradiation wavelengths are not limited to the IR and NIR portions of the spectrum, and can include light of shorter wavelength, such as light having wavelengths shorter than about 600 nanometers. Monochromatic light having a wavelength in the range from about 600-800 nanometers is suitable for Raman spectral analysis of tissue, for example. Longer illumination wavelengths will, generally, induce less background fluorescence in tissues (i.e., reducing the need to remove or correct for fluorescently-emitted radiation emitted from the tissue), but can decrease the intensity of Raman scattered radiation. Selection of an appropriate illumination wavelength is within the level of ordinary skill, taking into account the optical characteristics (e.g., fluorescence, scattering, and absorption) of the tissue(s) and tissue component(s) being assessed.

An advantage of using NIR radiation in the methods described herein is that it penetrates biological tissues more deeply than visible light so as to enable assessment of tissue and components lying farther from the sample surface than is possible using shorter wavelengths. Appropriate selection of optical probe placement site can reduce the need for deeply-penetrating irradiation. For example, for non-invasive analysis of a blood component, placement of the probe against a vascularized and preferably non-dermal, non-keratinized epithelial surface alleviates the need for NIR irradiation in many instances. In view of the increased noise and interference that can be expected to result from analysis of deeply-penetrating radiation, it is preferable to use an optical probe that is placed as close as possible (preferably in contact with) the tissue of interest.

The radiation source can optionally be coupled with one or more lenses, beam splitters, diffraction gratings, polarization filters, bandpass filters, or other optical elements selected for illuminating the sample surface in a desired manner. Such optical elements and methods of coupling them with radiation sources are known in the art.

The devices described herein preferably include a radiation source selected for its suitability for analysis using the device. Alternatively, a device can be designed to analyze a sample using ordinary sunlight or other ambient light, such as residential lighting or an illuminating instrument ordinarily found in a doctor's office.

Optical Illumination Fibers

The surface or body location illuminated by the radiation source can be directly irradiated, that is by radiation transmitted through the air interposed between the radiation source and the sample surface. Alternatively, radiation from the source can be transmitted to the sample surface by way of one or more optical fibers. The one or more fibers can be used to illuminate the surface continuously or intermittently over a portion that includes all of the regions assessed in the manner described below. Alternatively, one or more illuminating fibers can be used to irradiate discrete (adjacent or non-adjacent) regions of the sample surface, and some or all of those irradiated regions can be assessed in the manner described below. Devices and methods for coupling optical fibers with radiation sources are known in the art.

In one embodiment, one or more optical fibers used to illuminate the sample are bundled together with one or more optical detection fibers used to collect radiation reflected, emitted, or scattered from the tissue or its surface. Discrete bundles of illumination and detection fibers can be directed to selected areas of the sample surface (e.g., the bundles fixed in a selected geometric configuration and the ends of the bundles applied to or near the surface). The illumination fibers in each bundle can transmit light to the corresponding selected area of the surface, and light reflected, emitted, or scattered from that area of the surface can be collected by the detection fibers. Depending on the nature of the sample, light transmitted to the surface from the illumination fiber can pass through the surface and be reflected, scattered, or absorbed and emitted by one or more elements below the surface within the sample. By way of example, light can penetrate the surface of animal or plant tissues and reach cells or other structures which lie below the tissue surface. Interactions of subsurface structures with light transmitted through the surface can be assessed using light transmitted back through the surface (or through a different surface of the sample) and collected by detection fibers. Light transmitted by the detection fibers of each bundle can be assessed in a combined or discrete fashion, as desired.

The optical illumination fibers can optionally be coupled with one or more lenses, beam splitters, diffraction gratings, polarization filters, bandpass filters, or other optical elements selected for illuminating the sample surface in a desired manner. Such optical elements and methods of coupling them with optical fibers are known in the art.

Detectors

Light is collected from the assessed regions of the vascularized surface of the animal and transmitted to one or more detectors. Preferably a single detector is employed.

It is important that light be transmitted from the surface to the detector in a "mappable" or "addressable" fashion, such that light transmitted from different assessed regions of the body can be differentiated by the detector. Differentiation of light from discrete assessed regions can be achieved by simultaneously transmitting light from the regions to discrete portions (i.e., one or more detection elements) of the detector. Such differentiation can also be achieved by transmitting light from discrete regions to a single portion of the detector, so long as the light from the discrete regions can be differentiated, such as by sampling different regions over time. Preferably, light from discrete assessed regions of a sample surface is transmitted separately to discrete portions of a detector having a linear or two-dimensional array of detector elements.

It is not necessary that the correspondence between a portion of a detector and the portion of the sample surface from which light is transmitted to that detector portion be known. The methods and devices described herein can be used so long as the correspondence between the detector element(s) and a portion of the sample surface is the same for assessment of the optical characteristic of blood and the optical characteristic(s) of a blood component. Likewise, there is no requirement that the relative two-dimensional locations of assessed regions on the sample surface be preserved on the corresponding portions of, for example, a two-dimensional array of detector elements in a detector. If an image showing the optical characteristic of the tissue of interest or of a component of that tissue is desired to correspond to the two-dimensional appearance of the surface, then the relative positions of the assessed regions must be reflected in the relative positions of the detector elements (if not in the same geometric pattern, then at least in a decodable pattern whereby the geometric arrangement of assessed regions can be reconstructed from the geometric arrangement of corresponding detector elements). By way of example, a coherent array of bundled optical fibers can be used to correlate assessed regions of a surface with corresponding regions of an image.

The detector(s) must be able to detect at least two types of optical signals. Preferably a detector capable of detecting both signals is used. First, the detector (hereafter referred to in the singular in this section, regardless of whether one or more detectors is used) must be able to detect a first optical characteristic of the tissue of interest. Second, the detector must be able to detect a second optical characteristic of the selected component of the tissue. In the methods described herein, the selected tissue component is assessed by detecting the second characteristic only for assessed regions that exhibit the first characteristic. In this way, assessment of the selected tissue component is performed only in tissues characterized by the presence of detectable tissue of interest.

Light detected by the detector can be light transmitted, reflected, emitted, or scattered by the tissue through air interposed between the tissue surface and the detector. Alternatively, the light can be transmitted by way of one or more optical fibers to the detector. Regardless of whether an optical fiber is employed, one or more other optical elements can be interposed between the surface and the detector(s). If optical elements are used to facilitate transmission from the surface to the detectors, any other optical element(s) can be optically coupled with the fibers on either end or in the middle of such fibers. Examples of suitable optical elements include one or more lenses, beam splitters, diffraction gratings, polarization filters, bandpass filters, or other optical elements selected for transmitting or modifying light to be assessed by the detectors. Selection of one or more appropriate optical elements and coupling of such elements with a detector and, optionally optical fibers, is within the ordinary level of skill in this field.

By way of example, it is known that it is beneficial to use an optical element such as a filter, an interferometer or a dispersive spectrometer to detect Raman-shifted radiation scattered by a sample. For example, a suitable filter can be a cut-off filter, a Fabry Perot angle tuned filter, an acousto-optic tunable filter, a liquid crystal tunable filter, a Lyot filter, an Evans split element liquid crystal tunable filter, a Solc liquid crystal tunable filter, or a liquid crystal Fabry Perot tunable filter. Suitable interferometers include a polarization-independent imaging interferometer, a Michelson interferometer, a Sagnac interferometer, a Twynam-Green interferometer, a Mach-Zehnder interferometer, and a tunable Fabry Perot interferometer.

The construction and operation of the detector is not critical, so long as the detector is able to detect the relevant optical characteristic(s) described herein. Many suitable detectors are known in the art. It is also known that detectors suitable for detecting certain relatively weak optical emissions (e.g., Raman-shifted scattered radiation) can require highly sensitive detectors, such as charge-coupled device (CCD) detectors.

The detector is coupled with a controller of substantially any type suitable for operation of the detector. The controller can be a program operable on a personal computer, for example, or it can be a component of a free-standing apparatus (e.g., a spectrometer) that includes the detector. Optionally, the controller can operate other components of the device, such as a filter or a dispersive spectrometer.

In one embodiment, one or more optical fibers used to illuminate the sample are bundled together with one or more optical detection fibers used to collect radiation reflected, emitted, or scattered from the surface. Discrete bundles of illumination and detection fibers can be directed to selected areas of the sample surface (e.g., the bundles fixed in a selected geometric configuration and the ends of the bundles applied to or near the surface). The illumination fibers in each bundle transmit light to the corresponding selected area of the surface, and light reflected, emitted, or scattered from that area of the surface is collected by the detection fibers. Light transmitted by the detection fibers of each bundle assessed in a combined or discrete fashion, as desired.

In another embodiment, assessed regions of the sample surface correspond to the areas from which individual optical detection fibers collect light, and the light transmitted by each detection fiber is assessed separately.

The assessed regions can together represent only a portion of the area of the viewing field. It has been discovered that sampling the viewing field at points representing a minority of the total area of the field (e.g., at two, four, ten, fifty, one hundred, or more regions representing, in sum, 25%, 5%, 1%, or less of the field) can yield accurate results. The shape of assessed regions is not critical. For example, circular, annular, oval, square, or rectangular regions can be assessed, as can the area (however shaped) from which light is collected by a single detection fiber. Assessed regions can be adjacent one another, with no non-assessed region interposed between the adjacent assessed regions, whereby a substantially continuous patch or area of a tissue surface can be assessed. Assessed regions which do not exhibit an optical characteristic of the tissue of interest can be ignored for further analysis.

The area corresponding to each assessed region can be selected or generated in a variety of known ways. By way of example, a confocal mask or diffracting optical element placed in the illumination or collection optical path can limit illumination or collection to certain portions of the sample having a defined geometric relationship. Further by way of example, a plurality of regions can be assessed using a detector comprising a linear array of detector elements or a detector optically coupled with a linear array of optical fibers.

The number of regions of the sample surface that are assessed is not critical. The maximum number of regions on a sample surface that can be assessed using a single multi-element detector will be determined by the number of detector units in the detector, the resolution and sensitivity of the detector and its associated optics, the sample size, the size of the assessed regions, the intensities and wavelengths of the light used for illumination and analysis, and other characteristics that are understood by the ordinary worker in this field. At least three regions should be assessed for occurrence of a first optical property—one characteristic of the tissue of interest (i.e., occurrence of that first characteristic indicating that the tissue of interest is associated with the region). Preferably, more (e.g., six, ten, twenty, or fifty or more) regions are assessed for occurrence of the first characteristic. A second optical property—one characteristic of the tissue component to be analyzed—is assessed for at least one region at which the first characteristic occurs. Confidence in the assessment of the component in the tissue of interest can be increased by assessing the second property at multiple regions that exhibit the first characteristic.

Optical characteristics by which a tissue of interest can be differentiated from other tissues are known in the art. Selection of an appropriate characteristic for differentiating relatively tissues can depend on the type and nature of the tissue(s), and is within the level of skill of the ordinary artisan in this field. Examples of optical properties of tissues that can be used to distinguish them include reflectance and Raman scattering characteristics. For example, for blood, these properties include:

i) the reflectance attributable to hemoglobin around a wavelength of about 700 nanometers (see, e.g., Solenenko et al., 2002, Phys. Med. Biol. 47:857-873);

ii) the Raman scattering peak near 1365 cm$^{-1}$ attributable to hemoglobin (this peak is nearer 1355 cm$^{-1}$ for deoxygenated hemoglobin and is nearer 1380 cm$^{-1}$ for oxygenated hemoglobin)

Optical characteristics by which a component of a tissue can be assessed are known in the art. By way of example, Raman spectra of common blood constituents are disclosed in Enejder et al. (2002, Optics Lett. 27(22):2004-2006), in U.S. Pat. No. 5,615,673, and in U.S. Patent Application Publication no. 2005/0043597. NIR spectra of blood components are also reported in the literature. Use of this information to identify and quantify components in a sample is within the level of ordinary skill in this field. Examples of blood components that can be detected by Raman spectroscopy include glucose, creatine, lactic acid, carbon dioxide, and K, Mg, Na, Ca, and Cl ion complexes. Examples of blood components that can be detected by NIR spectroscopy include oxygenated and deoxygenated forms of hemoglobin. The methods described herein are not limited to assessment of blood components, but can be used to assess any optically-assessable compound, structure, or molecular state.

The methods and devices described herein can be used to detect normal components of tissues and substances that do not naturally occur in the tissues of a healthy individual. By way of example, the presence, concentration, or both of a drug can be assessed in an individual's tissue. Further by way of example, metabolites associated with occurrence of a disorder in a patient (e.g., acetone in muscle and blood of patients afflicted with ketoacidosis) and pathogens (e.g., bacterial toxins, bacterial cells, and viruses) can also be detected in an individual's tissues. By assessing a Raman or NIR characteristic of red blood cells in an individual's blood, the individual's hematocrit can be assessed. Assessment of oxidized and reduced forms of electron chain components can indicate the redox state of cells.

Light collected from multiple assessed regions of the sample can be combined prior to assessment of the optical property characteristic of the component. By way of example, light from all assessed regions that exhibits an optical property characteristic of a tissue of interest can be combined and the combined light can be assessed for the optical property of a component of that tissue. Alternatively, assessed regions which exhibits an optical property characteristic of a tissue of interest can be identified, and the light from each of those regions can be separately assessed for the optical property of the tissue component.

Multiple detectors can be used in the methods and devices described herein (e.g., one for detecting the optical characteristic of the tissue of interest and another for detecting the optical characteristic(s) of the tissue component). If multiple detectors are used, then detection elements of detectors for different optical properties should be correlated such that detection elements receiving radiation from common assessed regions can be identified. In that way, occurrence (or magnitude or non-occurrence) of an optical property of the tissue of interest at an assessed region can be used to determine whether an optical property of a tissue component from the same region should be assessed or recorded, for example. Use of a single, multi-purpose detector eliminates the need for such correlation. A detector having detection elements capable of detecting both radiation corresponding to an optical property of the tissue of interest and radiation corresponding to one or more optical properties of a tissue component thus eliminates the need for multiple detectors. A CCD detector capable of detecting both light reflected by the tissue of interest and Raman-shifted light scattered by a particular tissue component is an example of a suitable detector.

Spectroscopic Analysis of a Blood Component

In one embodiment, the methods and devices described herein can be used to identify portions of an animal tissue surface that contain (or are relatively rich in) blood and to analyze one or more components of the blood in those portions. In many instances, blood can be distinguished from other biological tissues relatively simply. By way of example, assessment of reflected radiation can be used to identify regions of a tissue surface associated with blood (i.e., a surface overlying one or more blood vessels or overlying a tissue containing pooled blood). Once regions of a tissue surface associated with blood have been identified, further assessment of those regions can be performed to specifically identify, quantify, or both identify and quantify a component of blood associated with those regions.

The spectroscopic method used to assess the blood component is not critical. Certain blood components (e.g., oxidized hemoglobin) have characteristic optical properties that can be assessed relatively simply, such as by assuming that all of an optical property that is detected is attributable to the component. However, assessment of many individual blood components (e.g., glucose, urea, or lactic acid) can be subject to significant interference from other compounds associated with the region. In order to differentiate the blood component of interest from other compounds that may be present, use of spectroscopic techniques that are able to distinguish the component from other compounds should be used.

Examples of highly specific spectroscopic techniques include Raman spectroscopy and IR spectroscopy. NIR spectroscopy has sufficient specificity for use in certain situations, such as differentiation of oxygenated and deoxygenated hemoglobin. Each of these techniques is known to be useful for correlating the presence of a specific compound with one or more detectable optical properties of that compound. Raman spectroscopy often provides more information regarding the identity of imaged materials than many other forms of spectroscopic analysis, so inclusion of Raman spectroscopy in the methods is preferred.

In an embodiment of the methods described herein, an optically detectable compound (e.g., a fluorescent dye or a compound with an easily-detected Raman scattering characteristic) can be added to the blood of a subject prior to performing the methods described herein. Detection of the compound can indicate assessed regions of the vascularized surface overlying blood-containing vessels or tissues. Relatively blood-rich portions of the surface can be identified in this way, and an optical characteristic of the blood component of interest can be assessed from one or more of those portions. Examples of suitable fluorescent dyes that can be used in this manner include known angiography dyes such as fluorescein and indocyanine green.

In addition to blood component-specific spectroscopic techniques, other spectroscopic measurements (e.g., absorbance, fluorescence, and/or refraction) can be performed to assess one or more of the regions sampled by the specific technique. This information can be used alone or as a supplement to the component-specific spectral information to further characterize the regions of the sample surface. This information can also be used to reduce the number of relatively blood-rich regions at which the component-specific spectral analysis is performed, particularly if the concentration of the blood component is expected to be non-homogenous in blood and one desires to assess such non-homogeneity.

Spectroscopic analysis of multiple regions of a tissue surface allows high quality spectral sensing and analysis without the need to perform spectral imaging at every assessed region of a surface. The regions corresponding to the presence of blood can be identified simply, and spectral analysis confined to those regions. Optical imaging can be performed on the sample surface (e.g., simultaneously or separately) and the optical image can be combined with selected blood component-specific spectrum information to define and locate regions of interest. Rapidly obtaining spectra from sufficient different locations of this region of interest at one time allows highly efficient and accurate spectral analysis and the identification of materials such as thrombi or pathogenic agents in blood.

Because a plurality of chemical compounds occur in blood and other tissues, it can be necessary to distinguish spectral features of the blood component of interest from overlapping spectral features of one or more other compounds. Any of a variety of known methods can be used to correlate the spectrum obtained at any particular point with reference spectra collected or stored in a memory unit for the compounds. By way of example, standard spectral library comparison methods can be used or the spectral unmixing methods described in U.S. patent application Ser. No. 10/812,233, filed 29 Mar. 2004 can be used. Sampling multiple regions of a sample surface allows variations in the spectra collected from the regions to be observed. Distinctions can be made as to components present in the various regions of the sample. By way of example, it can be assumed that a component having spectral features that do not vary in proportion to the relative amount of blood present at the assessed region are not representative of the chemical composition of blood, and can be considered background. For this region, it can be advantageous to assess optical properties of a tissue region that is determined to be relatively blood-poor or free of blood.

Correlative multivariate routines can be applied to spectral information collected from samples intentionally seeded with a known standard material (e.g., a component deliberately added to blood in a known amount). This approach incorporates calibration standards within spectral information collected from a sample and permits quantitative chemical analysis.

Spectroscopic Analysis of a Component of a Tissue other than Blood

The methods and devices described herein can also be used to identify portions of an animal tissue that contain (e.g., are, include, or overlie) a tissue other than blood. Examples of such tissues include epithelia, skeletal, smooth, and heart muscles, nerves, brain, blood vessel walls, liver, pancreas, peritoneal membrane, ovary, connective tissues (e.g., tendons and ligaments), and lymph nodes and vessels. The methods and devices can also be used to detect and analyze the contents of tissue-enclosed spaces, such as the interior of hair follicles, sweat glands, tissue inclusions, lipid bodies, pustules, blisters, subdermal necrotic regions, mucoids secreted by goblet cells, the gall bladder, the pancreas, and the like. In each instance, a first optical characteristic can be used to identify irradiated regions that correspond to the tissue or space of interest. A second optical characteristic of the identified regions (or of a component present at those regions) can be assessed if desired.

The penetrating capacity of illuminating light depends on the intensity of the light, the wavelength of the illuminating radiation, and the type(s) of tissue through which the light must penetrate, and these relationships are known in the art. By way of example, ultraviolet light is not expected to penetrate significantly beyond a tissue depth of several microns for most tissue types, while visible light can be expected to penetrate tens or thousands of microns, depending on the tissue type, and infrared light can be expected to penetrate millimeters or centimeters into various tissue types. The methods described herein can be used to detect tissues and their components that occur beneath at such a distance from the optical probe that the tissue can be irradiated and the relevant optical characteristic determined. At body locations characterized by the presence of multiple tissue types, noise and interference can increase with distance of the assessed tissue from the probe. For such locations, it is preferable to assess tissues located in contact with or very nearly opposed to the probe using radiation having a penetrating capacity as low as necessary for effective assessment.

By way of example, a device described herein can be applied to a skin surface (or to the oral surface of a human cheek or lip). The surface can be irradiated with near infrared (NIR) radiation. NIR reflected from multiple regions of the surface can be assessed, and such assessment will reveal that some of the regions are relatively blood-rich and that other regions exhibit reflectance characteristics more nearly characteristic of muscle. By way of example, differential NIR reflectance characteristics of hemoglobin and myoglobin can be used to make this assessment as described by Schenkman et al., 1999, Appl. Spectrosc. 53(3):325-331. Once blood-rich and muscle-rich regions of the surface have been identified, the blood rich regions may be further analyzed for components of blood.

NIR Spectroscopy

NIR spectroscopy is a mature, non-contact, non-destructive analytical characterization tool that has wide applicability to a broad range of compounds. The NIR region of the electromagnetic spectrum encompasses radiation with wavelengths of about 0.78 to 2.5 micrometers (i.e., radiation with wavenumbers of 12,800 to 4,000 inverse centimeters, i.e., 12,800 to 4,000 $cm^{-1}$). NIR spectra result from the overtone and combination bands of fundamental mid-infrared (MIR) bands.

NIR-based spectroscopy can be used to rapidly obtain both qualitative and quantitative compositional information about the molecular composition of a material such as blood. NIR microscopes or spectrometers can be used to obtain NIR absorption, emission, transmittance, reflectance, or elastic scattering data at a single wavelength or over a spectrum of wavelengths. NIR absorption data (e.g., a spectrum) can be collected in transmittance, scattering, or reflectance mode.

NIR detectors have been used by others prior to this disclosure. By using optical filters (e.g., cold filters) to block visible wavelengths (ca. 0.4 to 0.78 micrometers), charge-coupled devices (CCDs, such as those used in digital cameras and camcorders) can be used to detect NIR light to wavelengths around 1100 nanometers. Other regions of the NIR spectrum can be viewed using devices such as indium gallium arsenide (InGaAs; ca. 0.9 to 1.7 micrometers) and indium antimonide (InSb; ca. 1.0 to 5.0 micrometers) focal plane array (FPA) detectors. Integrated wavelength NIR imaging allow study of relative light intensities of materials over broad ranges of the NIR spectrum. However, useful NIR spectral information can be unattainable without some type of discrete wavelength filtering device.

The use of dielectric interference filters in combination with NIR FPAs is one method in which NIR spectral information can be obtained from an assessed region of a sample surface. To generate NIR spectral information, a NIR light beam is defocused to illuminate multiple regions of the sample surface (i.e., either individually, or by broad illumination of the surface) and the reflected, transmitted, or elastically scattered light from the illuminated area is transmitted to an NIR detector. A selection of discrete dielectric interference filters (provided in a filter wheel or in a linearly- or circularly-variable format) can be positioned in front of a broadband NIR light source, or in front of the NIR FPA (i.e., between the illuminated area and the FPA) in order to collect NIR wavelength-resolved spectral information. Typically, the use of several fixed bandpass filters is required to access the entire NIR spectrum. Key limitations of the dielectric filter approach include the need for a multitude of discrete filters to provide appreciable free spectral range, and the reliance on moving mechanical parts in continuously tunable dielectric interference filters as a requirement to assess wavelength-resolved features. Although moving mechanical assemblies can be engineered, they add significant cost and complexity to NIR spectral analysis systems. Alternatives to moving mechanical assemblies can be more cost effective and provide performance advantages.

Acousto-optic tunable filters (AOTFs) have been employed in NIR spectrometers with substantially no moving parts. The AOTF is a solid-state device that is capable of filtering wavelengths from the UV to the mid-IR bands, depending on the choice of the filter's crystal material. Operation of an AOTF is based on interaction of light with a traveling acoustic sound wave in an anisotropic crystal medium. Incident light is diffracted with a narrow spectral bandpass when a radio frequency signal is applied to the device. By changing the applied radio frequency (which can be under computer control, for example), the spectral passband can be tuned rapidly and without moving parts. The methods and devices described herein are not limited to those using an AOTF. Numerous other optical filtering technologies (e.g., liquid crystal tunable filters, photonic crystals, spectral diversity filters, and fiber array spectral translators) are available and can be employed as desired by a skilled artisan in this field.

Raman Spectroscopy

Raman spectroscopy provides information about the vibrational state of molecules. Many molecules have atomic bonds capable of existing in a number of vibrational states. Such a molecule is able to absorb incident radiation that matches a transition between two of its allowed vibrational states and to subsequently emit the radiation. These vibrational transitions exhibit characteristic energies that permit definition and characterization of the bonds that are present in a compound. Analysis of vibrational transitions therefore permits spectroscopic molecular identification.

Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The energy difference is consumed by a transition between allowable vibrational states, and these vibrational transitions exhibit characteristic values for particular chemical bonds, which accounts for the specificity of vibrational spectroscopies such as Raman spectroscopy.

The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in frequency can be more easily distinguished from the Rayleigh scattered light.

Because Raman spectroscopy is based on irradiation of a sample and detection of scattered radiation, it can be employed non-invasively and non-destructively, such that it is suitable for analysis of biological samples in situ. Water exhibits relatively little Raman scattering (e.g., water exhibits significantly less Raman scattering than infrared absorbance), and Raman spectroscopy techniques can be readily performed in aqueous environments. Raman spectral analysis can be used to assess occurrence of and to quantify blood components and components of other tissues.

The Raman spectrum of a material can reveal the molecular composition of the material, including the specific functional groups present in organic and inorganic molecules. Raman spectroscopy is useful for detection of metabolites, pathogens, and pharmaceutical and other chemical agents because most, if not all, of these agents exhibit characteristic 'fingerprint' Raman spectra, subject to various selection rules, by which the agent can be identified. Raman peak position, peak shape, and adherence to selection rules can be used to determine molecular (or cell) identity.

In the past several years, a number of key technologies have been introduced into wide use that have enabled scientists to largely overcome the problems inherent to Raman spectroscopy. These technologies include high efficiency solid-state lasers, efficient laser rejection filters, and silicon CCD detectors. In general, the wavelength and bandwidth of light used to illuminate the sample is not critical, so long as the other optical elements of the system operate in the same spectral range as the light source.

In order to detect Raman scattered light and to accurately determine the Raman shift of that light, the sample should be irradiated with substantially monochromatic light, such as light having a bandwidth not greater than about 1.3 nanometers, and preferably not greater than 1.0, 0.50, or 0.25 nanometer. Suitable sources include various lasers and polychromatic light source-monochromator combinations. It is recognized that the bandwidth of the irradiating light, the resolution of the wavelength resolving element(s), and the spectral range of the detector determine how well a spectral feature can be observed, detected, or distinguished from other spectral features. The combined properties of these elements (i.e., the light source, the filter, grating, or other mechanism used to distinguish Raman scattered light by wavelength) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light, grating groove density, slit width, interferometer stepping, and other factors) can limit the ability to resolve, detect, or distinguish spectral features. The skilled artisan understands that and how the separation and shape of Raman scattering signals can determine the acceptable limits of spectral resolution for the system for any of the Raman spectral features described herein.

Typically, a Raman peak that both is distinctive of the substance of interest and exhibits an acceptable signal-to-noise ratio will be selected. Multiple Raman shift values characteristic of the substance can be assessed, as can the shape of a Raman spectral region that may include multiple Raman peaks. If the sample includes unknown components, then the entire Raman spectrum can be scanned during spectral data acquisition, so that the contributions of any contaminants to the data can be assessed.

Devices

The invention includes devices for assessing a component of a tissue of an animal by the methods described herein. The device comprises a first detector for detecting an optical characteristic of each of multiple irradiated regions of the body of the animal. The multiple regions can have a predetermined geometric relationship, which need not be a regular pattern nor even invariant from surface to surface. It is sufficient that the regions retain their geometric relationship only long enough to permit correlation of optical properties of the tissue of interest and the tissue component for the regions. The device includes a controller that is operably linked to the detector. The controller restricts detection of the optical property(ies) of the tissue component to the regions that exhibit an optical characteristic of the tissue of interest.

The detectors used to assess an optical characteristic of a tissue and one or more optical properties of the tissue component can be, and preferably are, a single detector. Numerous suitable detectors are known in the art (e.g., CCD detectors), and selection of an appropriate detector is within the ken of the ordinarily skilled artisan in view of the disclosure herein.

The device can include a radiation source for irradiating the regions of the sample, either individually (e.g., using optical fibers to transmit light from the radiation source to the regions) or collectively (e.g., by irradiating two or more regions with radiation transmitted from the source or from an optical fiber optically coupled to the source). Multiple radiation sources can be included in (or packaged with) the device, each of the multiple sources irradiating some or all of the regions of the sample surface. Radiation sources which emit radiation of different wavelengths, for example, can be used where analytical techniques requiring such illumination is desired. Monochromatic or polychromatic lights sources can be used. Selection of an appropriate radiation source can be made by an ordinarily skilled artisan in view of the other components of the device, the spectral techniques employed, and the disclosure herein.

Light reflected, transmitted, emitted, or scattered (elastically or inelastically) from the sample surface is delivered to one or more detectors so that each region can be assessed for occurrence of an optical property characteristic of the tissue of interest and so that one or more regions that exhibit such a characteristic can be further assessed for occurrence, magnitude, or both, of one or more optical properties characteristic of the tissue component of interest. This light can be transmitted directly from the surface to the detector (e.g., using a detector that contacts the sample surface or has a layer of air or another substance interposed between it and the sample surface). The light can be transmitted from the surface to the detector using optical fibers along some or all of the gap between the surface and the detector.

One or more optical elements (other than, or in addition to, optical transmission fibers) can be optically coupled with the detector and interposed between the surface and the detector. Examples of appropriate elements include a lens, and an optical filter. For example, if the device employs Raman spectral analysis to assess occurrence of a tissue component, it can be advisable to filter light scattered from the sample surface to reduce (or preferably substantially eliminate) elastically scattered light from the radiation transmitted from the surface to the detector.

The device can include a computer memory unit for storing information (e.g., reference spectra) useful for correlating Raman-shifted radiation scattered from the regions with concentration of the blood component. The memory unit can also store relevant optical property information useful for comparison with data gathered from the sample for the purpose of identifying portions of the animal body at or near which the tissue of interest occurs. The device can also include a display (e.g., a numerical display) for indicating an optical characteristic of the sample or the concentration of a tissue component, for example. A power supply (e.g., a battery) can be incorporated into the device, or the device can be adapted for connection to an external power supply (e.g., it can have a plug suitable for insertion into a standard residential or commercial electrical wall socket).

EXAMPLES

The invention is now described with reference to the following Examples. These Examples are provided for the purpose of illustration only, and the invention is not limited to these Examples, but rather encompasses all variations which are evident as a result of the teaching provided herein.

Example 1

FIG. 1 is a schematic diagram of an embodiment of the non-invasive chemometric analysis device described herein. In FIG. 1, a probe 20 has a surface 22 that can be applied to a vascularized surface of an animal. Multiple holes 24 extend through the surface, through which radiation can pass (e.g., through air, a lens, or one or more optical fibers in the hole). In the embodiment shown in FIG. 1, optical fibers for illumination 40 are optically coupled with a radiation source 60 and pass through the holes 24 in the probe 20 to illuminate whatever lies adjacent the surface 22. Optical fibers 50 for collecting light reflected, emitted, or scattered from whatever lies adjacent the surface 22 are optically coupled to a detector 80, optionally by way of an optical element 70 such as a tunable filter or an interferometer. The detector 80 assesses light transmitted thereto by the optical fibers 50 to determine an optical property corresponding to discrete regions of space adjacent the surface 22 (e.g., each region corresponding to a single optical fiber or to a group of optical fibers). A computer processor or other controller 90 identifies regions for which the optical property is characteristic of blood, optionally storing them in a computer memory unit 110. Using light transmitted from the identified regions by way of the optical fibers 50, the detector 80 can assess a second optical property. In this manner, assessment of the second optical property can be limited to regions of space adjacent the surface 22 that exhibit an optical characteristic of blood. The second optical property can be used, for example, to assess the concentration of the component in the blood, and that concentration can be calculated by the computer processor 90 and stored in memory 110, displayed on a display 100, or both.

By way of example, the device illustrated in FIG. 1 can be used to assess blood glucose concentration in a human as follows. The surface 22 of the probe 20 is placed against a vascularized surface (e.g., skin or under the tongue) of the human. Radiation generated by the radiation source 60 passes through the illumination delivery fibers 40, whereby the vascularized surface is irradiated through multiples holes 24 in the surface 22 into or through which the fibers 40 pass. Light reflected from the human passes into optical fibers 50 that are present in or behind, or extend through, the holes 24. In this embodiment, a liquid crystal tunable filter 70 is tuned to pass light having a wavelength for which the reflectance characteristics of blood are known. The light passes to a CCD detector 80 at which the intensity of reflected light is assessed for multiple regions of the human. A computer 90 compares the intensity values with reference values stored in an operably connected computer memory unit 110. For each region for which the intensity value indicates the presence of a suitable amount of blood, the computer 90 causes the detector 80 to assess one or more optical properties of glucose, such as a Raman spectrum or the intensity of Raman-shifted radiation scattered from the region at Raman shift values characteristic of glucose. The second optical property(ies) can be stored in the memory 110 or used by the computer 90 to calculate a concentration of glucose in the blood.

Figure 3:
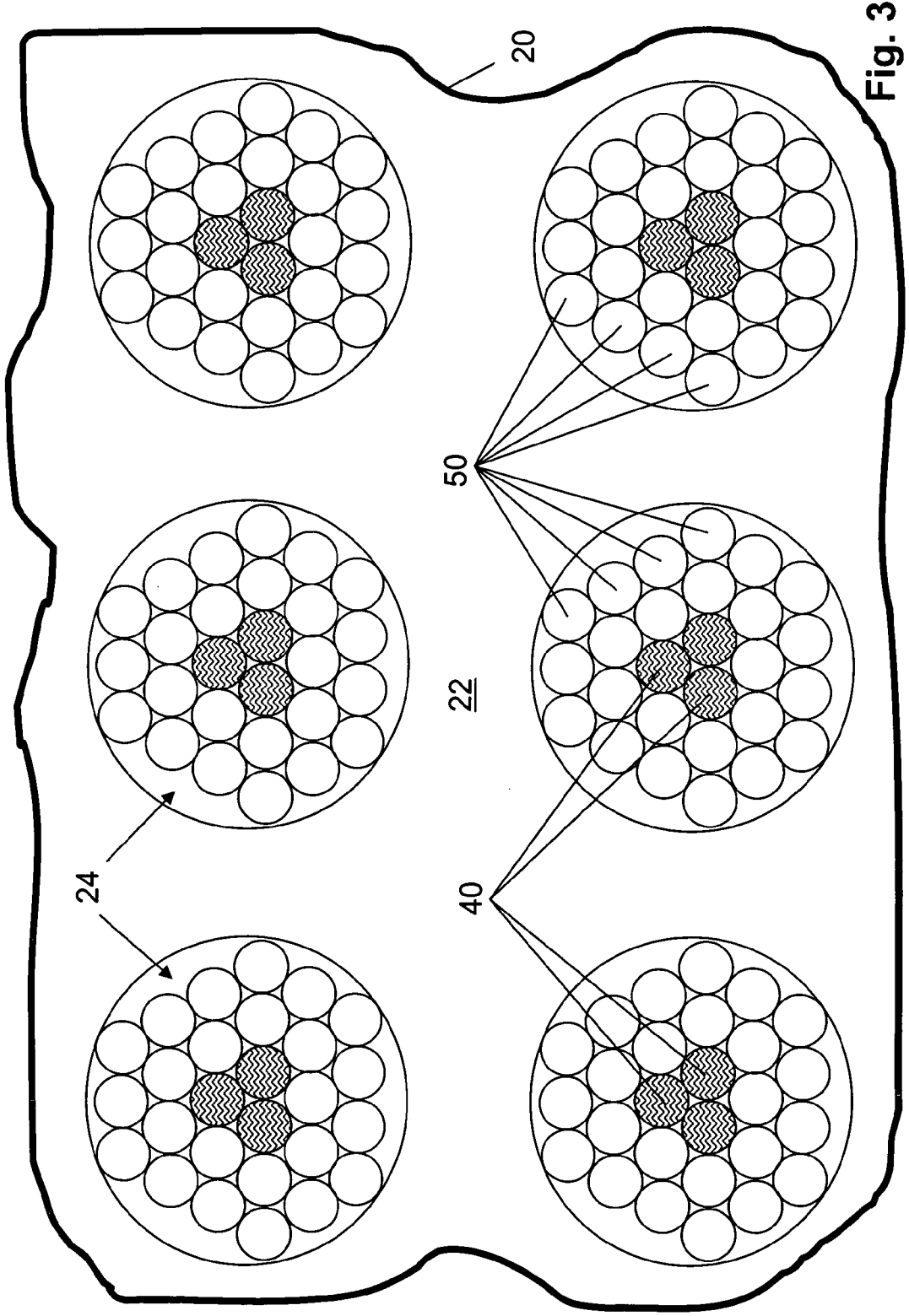
FIG. 3 is an example of a layout pattern for optical fibers and holes in a device described herein.
Figure 4:
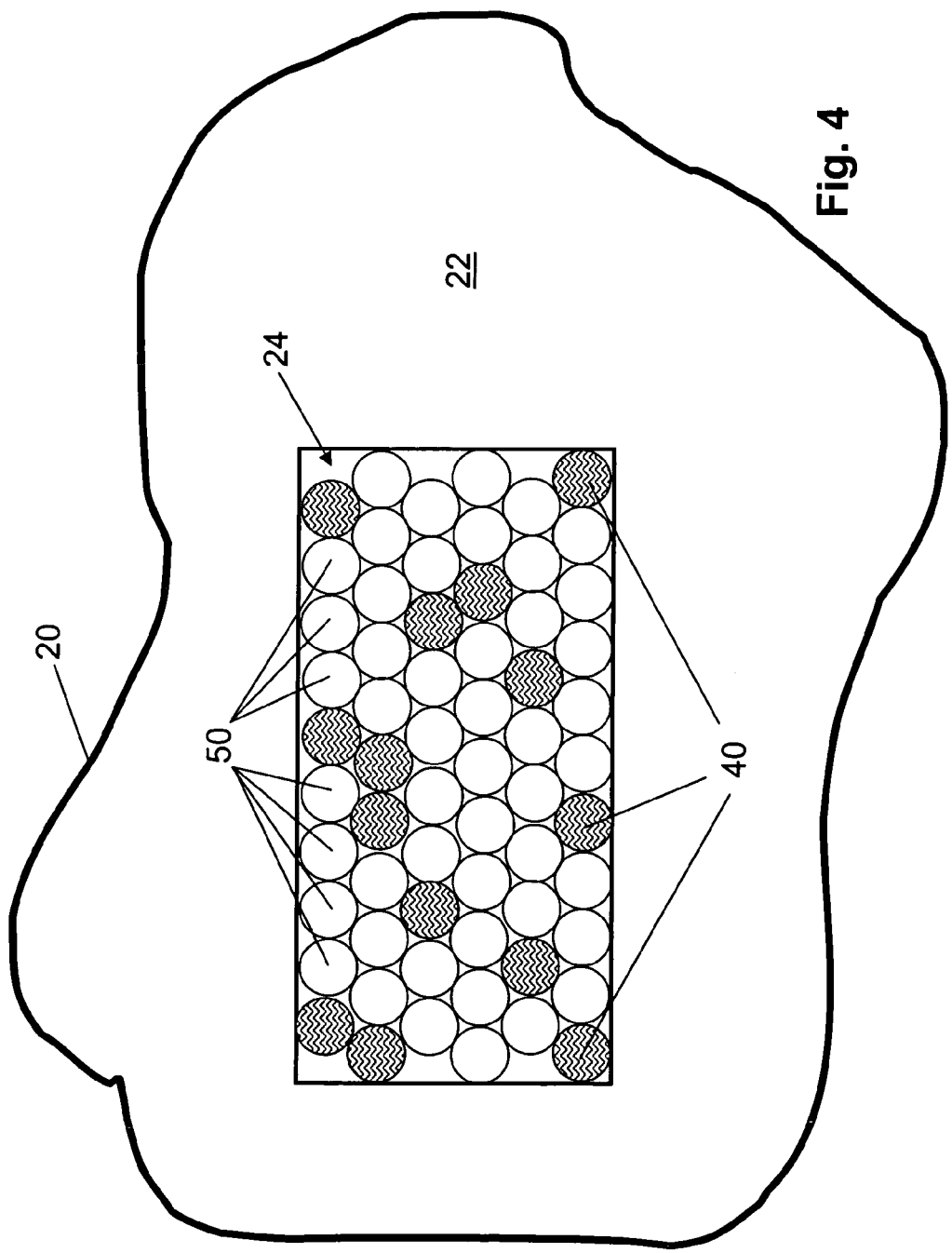
FIG. 4 is an example of a layout pattern for optical fibers in a device described herein.

In FIG. 1, the probe 20 is shown having holes 24 situated essentially randomly across the surface 22 thereof. Although the holes 24 can be arranged essentially randomly, they can also be arranged in a regular or irregular pattern. Each of FIGS. 2 and 3 illustrates an alternative layout of holes 24 across a cutaway portion of the surface 22 of the probe 20. In FIG. 2, five holes 24 of a regular pattern are shown, each hole 24 having nineteen optical fibers extending therethrough, including one centrally-situated optical fiber 40 for transmitting light onto the sample surface and eighteen optical fibers 50 circumferentially arranged around optical fiber 40 for collecting and transmitting light from the sample surface. In FIG. 3, six holes 24 of a regular pattern are shown, each hole 24 having twenty-three optical fibers extending therethrough, including three centrally-situated optical fibers 40 for transmitting light onto the sample surface and twenty optical fibers 50 circumferentially arranged around optical fibers 40 for collecting and transmitting light from the sample surface. However, the holes need not be round, nor need the fibers 40 and 50 be arranged in a regular pattern. For example, FIG. 4 illustrates a hole 24 in the surface 22 of the probe 20 in which fourteen illuminating fibers 40 and thirty-nine light-collecting fibers 50 are arranged in an essentially random array.

FIG. 5 illustrates two embodiments of how sample illuminating fibers 40 and light-collecting fibers 50 can be situated within holes 24 that extend through the surface 22 of the probe 20. In FIG. 5A, the ends of the illuminating fiber 40 and light-collecting fibers 50 are substantially flush with the surface 22. In FIG. 5B, the ends of fibers 40 and 50 are optically coupled with a lens 30.

Example 2

Blood Glucose Determination

The invention described herein provides an integrated method to perform a non-invasive, rapid measurement of the body chemistry of a conscious or unconscious person. The method involves using a small multipoint probe inserted under the tongue or into another vascularized tissue-lined body surface or cavity. The probe can perform several measurements simultaneously (e.g., under computer control) at several points without a need to move the probe.

Several features of the probe, where and how it is located and the laser excitation wavelength used, can be routinely optimized for Raman scattering assessment of glucose and other blood components. Known spectral unmixing and other software algorithms can be applied to the acquired Raman data and enhance the selectivity and sensitivity of the methods for detection and quantification of analytes. Such enhancements can improve the accuracy and reduce the time between sampling and production of an analysis report.

Diabetes is recognized as a widespread health problem. Blood glucose monitoring is critical for the treatment and medication of diabetes. Currently, glucose is usually monitored by breaking the skin to obtain a blood sample which is analyzed to determine relative concentrations of specific chemicals in the blood. Optical methods such as Raman and IR have the capability to quantitatively characterize the chemicals in the blood, but suffer when applied non-invasively (without penetration of the skin) due to a number of complicating factors. For example, past trans-epidermal approaches suffer from the need to use long wavelengths to penetrate the skin to detect chemicals or gases in the blood. Use of shorter wavelengths makes detection of optical signals more complex and costly. For Raman spectroscopy, the scattering cross sections at longer NIR wavelengths are significantly reduced relative to visible wavelengths, typically by a factor of 10. Long collection times for a large localized probe on a non-anesthetized patient is problematical, since normal movement of the patient will produce variations in signal intensities over time, and those variations distort spectral from the target area. In addition, variations in skin pigmentation can limit the interpretation of the chemical information obtained from many optical methods. Such pigmentation variations require specific calibration of detected components for each individual measured.

Much prior art is directed to using optical measurements to measure the analytes in blood or the composition of tissues removed from the body for the purpose of pathology. Use of NIR and infrared (IR) spectroscopy to detect blood gases and blood analytes non-invasively has been long pursued, without any evidence of commercially viable products.

The methods and devices described herein provide an integrated approach that optimizes Raman sample measurement and data analysis to minimize data measurement times and patient discomfort. Efficient Raman scattering analysis for specific target blood chemistry analytes can be obtained. The methods and devices permit a relatively non-skilled operator, such as a physician, a physician's assistant, a nurse, or a patient, to perform the data acquisition. In one embodiment, several points on a vascularized tissue surface are simultaneously measured using a series of high numerical aperture micro lens (i.e., ordinary lens or a fresnel lens) that are coupled to optical fibers for the delivery of excitation radiation and collection of Raman scattered light. The multipoint micro-lens sampling head and fiber optic optical delivery system comprise the detection probe which can be attached to a handheld detector or connected via a handheld extension to a portable source/detection/analysis station.

To avoid complications found from the optical properties and variability of the compounds in the skin, such as melanin, a compact, thermometer-like multipoint probe can be inserted into a "pink tissue" body cavity. The tissues lining the cavity under the tongue have are very thin epithelia, and multipoint sampling of these tissues can enhance illumination of blood rich tissues, such as blood vessels. Tissue lining the rectum is also rich in blood vessels and has a relatively thin epithelial lining. The geometry and orientation of the mouth and extremities of the tongue enable the probe a to be fixedly held in place for the duration of a measurement, and clamps, mouthpieces, or similar adapters can be used to enhance fixedness if necessary. The under-tongue region also has the advantage that it is a convenient and familiar location for the patient to hold a probe.

Example 3

Assessment of a Tissue Component in One or More Tissues

The devices described herein assess optical properties at multiple body locations. A plurality of tissue types can therefore be assessed simultaneously using the devices, the number of assessable tissues depending on the number of tissue types that are contacted by or in close opposition to a radiation-collecting optical conduit of the device. Careful placement of an optical probe described herein by a skilled operator can increase or decrease the likelihood that a particular tissue type will be contacted by the probe. Furthermore, if desired, probes can be constructed to maximize the likelihood that the probe will contact a tissue of interest when the probe is applied to or inserted into the body of an animal.

FIG. 6 illustrates assessment of one or more tissue components in multiple tissue types. The device used in the analysis illustrated in FIG. 6 includes an elongate probe 20 that, in FIG. 6, is emplaced in the body of an animal. The probe 20 has a plurality of lenses 30 along its length. Those lenses 30 contact, or are in close opposition to a variety of tissue types. Not shown in FIG. 6 are optical fibers extending along the length of the probe 20 which transmit radiation collected by lenses 30 to a detector.

In FIG. 6, lens 30-1 collects radiation from skin tissue S. Lens 30-2 collects radiation from sub-dermal connective tissue C. At least two lenses, 30-3 and 30-4, collect radiation from muscle tissue M. Lenses 30-5 and 30-6 collect radiation from venous V and arterial A capillaries which are located in close proximity to the lenses. Lens 30-7 collects radiation from several tissues, including muscle M and connective C tissues and from a fatty deposit F. To detect glucose in muscle cells, the device collects radiation from each of the lenses and assesses, for each lens, whether the collected radiation exhibits a first optical characteristic of muscle tissue. From lenses corresponding to muscle tissue (i.e., lenses 30-3, 30-4, and 30-7), the device also collects radiation and assesses that radiation for a second optical characteristic of glucose. Glucose in muscle tissue can be quantified by correlating the second optical characteristic of radiation collected from the lenses corresponding to muscle tissue using the known optical properties of glucose.

The preceding analysis included assessment of the second optical characteristic for radiation collected by lens 30-7, which collects radiation from muscle and two other tissues. An assessment of glucose more specific for muscle tissue can be obtained by excluding from the analysis radiation collected from body locations that exhibit both the first optical characteristic of muscle tissue and an optical characteristic of another tissue type. In this more specific assessment, only radiation collected from lenses 30-3 and 30-4 is assessed for the second optical characteristic of glucose.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of assessing a component of a tissue of an animal, the method comprising:
    irradiating a plurality of regions of the tissue to generate radiation therefrom;
    evaluating first optical data generated from each of said plurality of irradiated regions to identify at least one of said plurality of regions of tissue exhibiting a first optical characteristic of the tissue, said first optical characteristic associated with said first optical property;
    obtaining second optical data generated from said at least one identified region in said plurality of regions, wherein said first and said second optical data are generated by different spectroscopic modes, wherein the second optical data is generated by transmitting radiation, generated from said at least one identified region, through a filter, thereby obtaining filtered photons;
    assessing said component in said at least one identified region by evaluating said filtered photons for a second optical characteristic associated with said component; and
    reporting an identity for said component in accordance with a result of said accessing step.

2. The method of claim 1, wherein the component is assessed in the tissue in vivo.

3. The method of claim 1, wherein the second optical characteristic of the component is assessed for at least two identified regions.

4. The method of claim 1, wherein the second optical characteristic is a Raman shift of light scattered from the identified region that is attributable to the component.

5. The method of claim 1, wherein the first optical characteristics of the irradiated regions are assessed using multiple optical conduits that optically couple the irradiated regions with a detector.

6. The method of claim 5, wherein the conduits are optical fibers.

7. The method of claim 6, wherein the optical fibers are arranged in a coherent bundle.

8. The method of claim 5, wherein, for each irradiated region, the first and second optical characteristics are assessed using the same optical conduit.

9. The method of claim 5, wherein, for each irradiated region, the first and second optical characteristics are assessed using multiple optical conduits.

10. The method of claim 5, wherein the optical conduits extend along a probe inserted into the body of the animal.

11. The method of claim 5, wherein the optical conduits extend along a probe applied against a body surface of the animal.

12. The method of claim 5, wherein the optical conduits are rigidly fixed relative to one another.

13. The method of claim 1, wherein the component is a cell.

14. The method of claim 13, wherein the component is an abnormal cell of the tissue.

15. The method of claim 1, wherein the tissue comprises cells of multiple types.

16. The method of claim 1, wherein the regions are irradiated with substantially monochromatic light.

17. The method of claim 1, further comprising:
applying a spectral unmixing method to said second optical property to distinguish said second optical characteristic associated with said component from other optical characteristics associated with other components.

18. A device for assessing a component of a tissue of an animal in vivo, the device comprising a radiation source for irradiating multiple regions of an animal body, light being conveyed from the radiation source to each of the regions by at least one discrete optical illumination fiber for each region; a first detector for identifying regions that exhibit a first optical characteristic of the tissue, the first detector being optically coupled with the regions by way of at least one discrete optical detection fiber for each region; a second detector for assessing Raman-shifted radiation scattered by the identified regions, the second detector being optically coupled with the identified regions by way of at least one discrete optical detection fiber for each region, and there being an optical filter interposed between the second detector and the identified regions and; a computer processor operably linked to the second detector for restricting assessment of Raman-shifted scattered radiation to the identified regions and for correlating Raman-shifted radiation scattered by the identified regions with the quantity of the component in the tissue.

* * * * *